United States Patent [19]

Warthen et al.

[11] Patent Number: 4,798,200

[45] Date of Patent: Jan. 17, 1989

[54] SELF-ADHERING ORTHOPEDIC SPLINT

[75] Inventors: William P. Warthen, Spartanburg; Mohammed I. Akhawala, Simpsonville, both of S.C.

[73] Assignee: Milliken Research Corporation, Spartanburg, S.C.

[21] Appl. No.: 130,588

[22] Filed: Dec. 9, 1987

[51] Int. Cl.$^4$ .................................................. A61F 5/04
[52] U.S. Cl. ....................................................... 128/89 R
[58] Field of Search .............. 128/90, 89 R, 155, 169; 2/262, 275; 66/190, 192, 193, 202

[56] References Cited

U.S. PATENT DOCUMENTS

| | | | |
|---|---|---|---|
| 2,419,358 | 4/1947 | Lovell | 128/90 |
| 2,692,842 | 10/1954 | Dildilian | 66/193 |
| 2,711,168 | 6/1955 | Brickman et al. | 128/89 R |
| 3,536,072 | 10/1970 | Quello | 128/169 |
| 3,570,482 | 3/1971 | Emoto et al. | 66/193 |
| 3,612,265 | 10/1971 | Dickerson | 206/63.2 |
| 3,757,541 | 9/1973 | Fröhlich et al. | 66/193 |
| 3,787,272 | 1/1974 | Nisbet et al. | 128/90 |
| 3,888,247 | 6/1975 | Stenvall | 128/155 |
| 3,983,870 | 10/1976 | Herbert et al. | 128/165 |
| 3,985,128 | 10/1976 | Garwood et al. | 128/90 |
| 4,009,597 | 3/1977 | Wall et al. | 66/193 |
| 4,112,177 | 9/1978 | Salditt et al. | 428/304 |
| 4,177,812 | 12/1979 | Brown et al. | 128/284 |
| 4,244,199 | 1/1981 | Rhode | 66/193 |
| 4,286,586 | 9/1981 | Potts | 128/90 |
| 4,323,061 | 4/1982 | Usukura | 128/90 |
| 4,425,398 | 1/1984 | Berczi | 66/193 |
| 4,624,116 | 11/1986 | Rogers | 66/193 |
| 4,631,932 | 12/1986 | Sommers | 66/193 |
| 4,658,604 | 4/1987 | Wilson | 66/192 |
| 4,665,909 | 5/1987 | Trainor | 128/155 |

FOREIGN PATENT DOCUMENTS 2019248 10/1979 United Kingdom .

Primary Examiner—Robert A. Hafer
Assistant Examiner—Michael Brown
Attorney, Agent, or Firm—Terry T. Moyer; H. William Petry

[57] ABSTRACT

A self-adhering, orthopedic splint is provided which is capable of being conformed to the contours of a limb which comprises an elongated, warp knit fabric having relatively stiff, inelastic monofilaments in the width direction and relatively flexible, inelastic yarns in the length direction; the monofilaments are interrupted by at least one hinged section running in the lengthwise direction and the fabric is provided with a normally tacky, pressure sensitive adhesive.

6 Claims, 3 Drawing Sheets

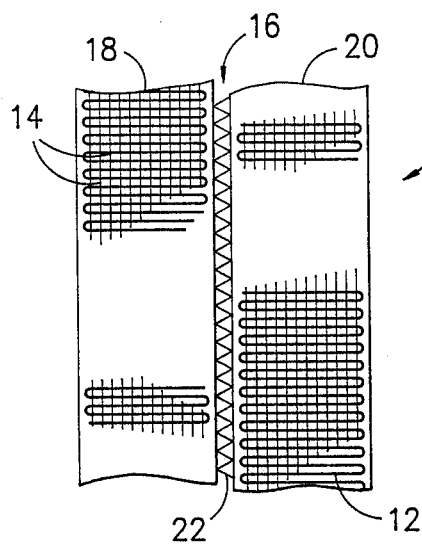
FIG. -1-
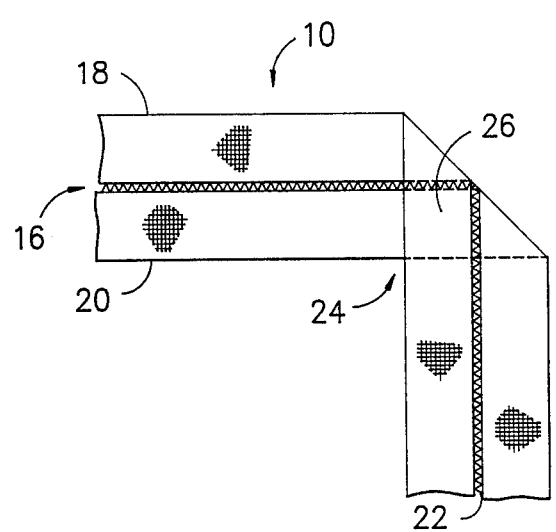
FIG. -2-
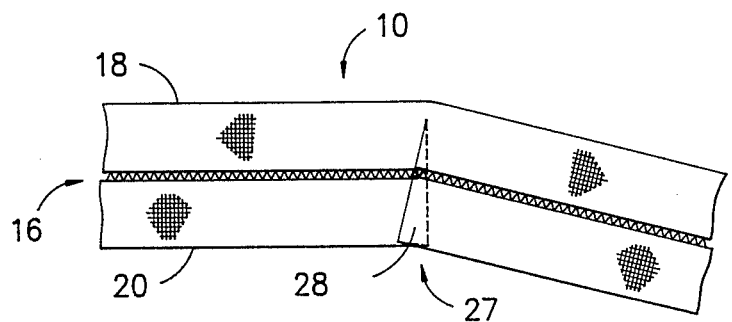
FIG. -3-
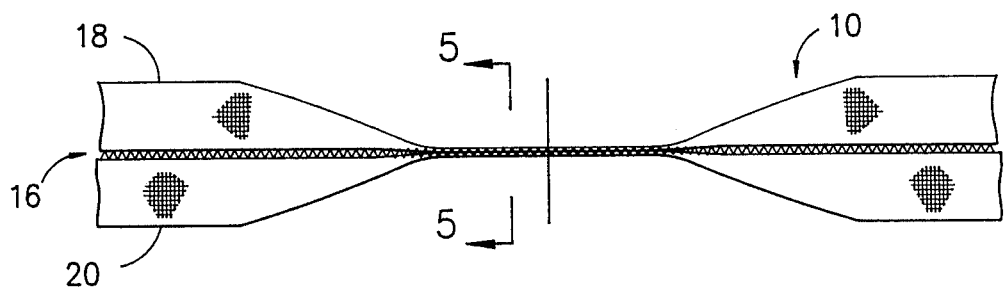
FIG. -4-
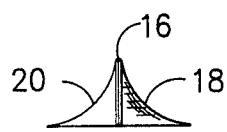
FIG. -5-

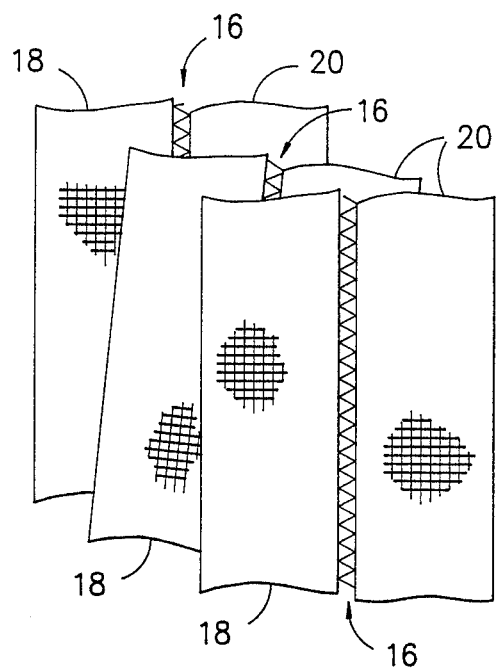
FIG. -6-
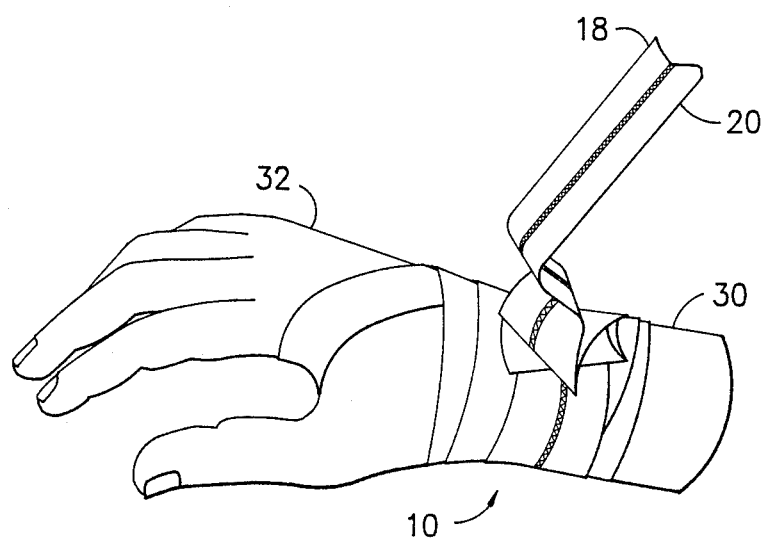
FIG. -7-

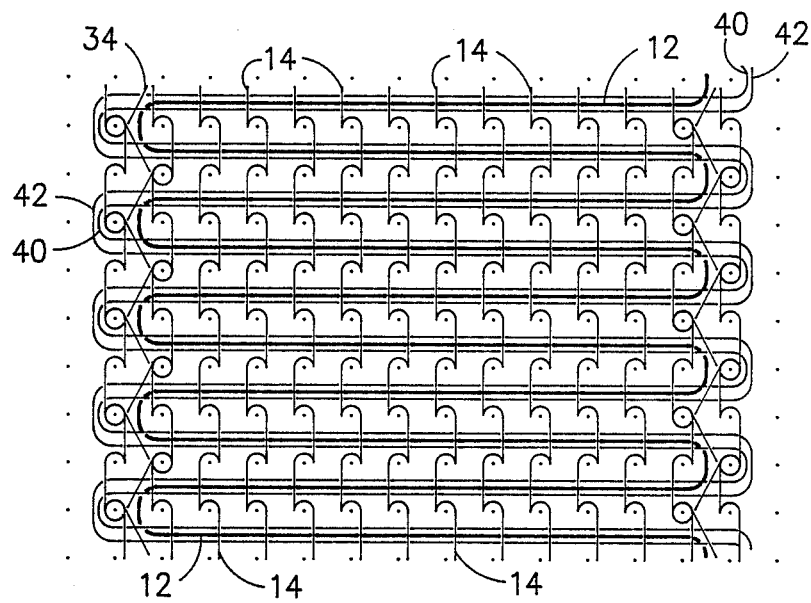
FIG. −8−
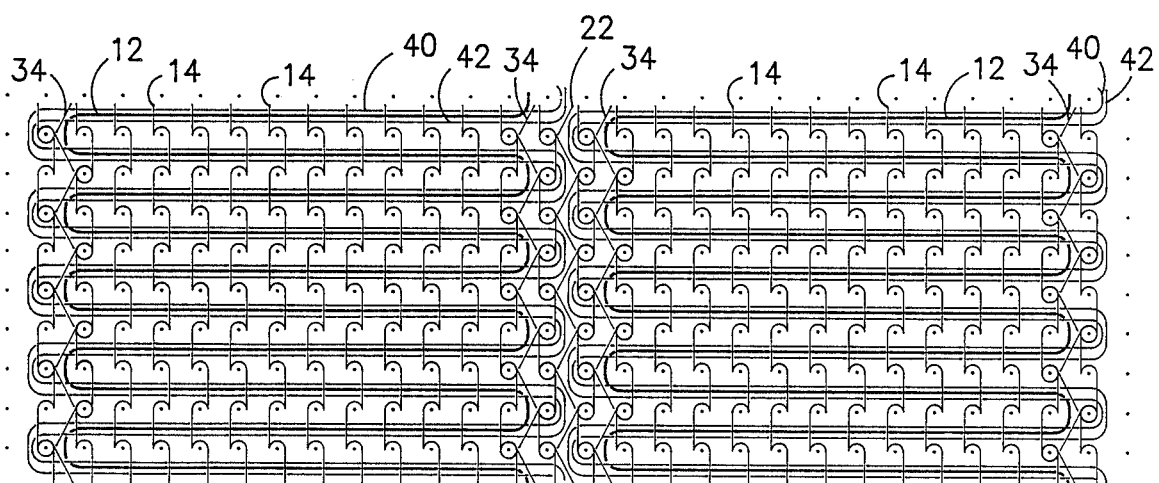
FIG. −9−

SELF-ADHERING ORTHOPEDIC SPLINT

The present invention relates to a self-adhering being conformed to the contours of a limb.

Conventionally today, where injuries such as sprains or fractures occur to a limb, physicians have several options for treatment. Serious fractures are typically treated by means of a cast which is a bandage impregnated with a hardenable material which, when hardened, totally immobilizes the limb or affected joint area. Less serious injuries such as minor fractures and sprains may be treated either by simply wrapping the affected area of the limb with conventional adhesive tape or by wrapping it with an elastic bandage.

All of these alternative treatment methods have disadvantages. Casts result in total immobilization which may not be necessary for certain injuries They also cannot be removed and replaced easily where, for instance, periodic bathing of the affected limb may be desired. Casts also tend to be bulky cumbersome for the patient.

Adhesive tape may initially provide some support but after some initial flexing the desired rigidity may not be retained. They are also hot and interfere with transepidermal water loss. Elastic bandages, which are made with relatively elastic yarns that are stretched over the affected area, actually provide very little support to affected limbs and joints. In addition, they are hot, tend to interrupt circulation, and interfere with transepidermal water loss.

By contrast to the known treatment techniques, the orthopedic splints of the present invention may provide improved support and may be used without compromising circulation to the affected area. The orthopedic splints of the present invention may also be more breathable and hence provide more comfort to the wearer and may be used without interrupting transepidermal water loss. Furthermore, the splints of the present invention are engineered to provide excellent conformity to any affected limb or joint. The splints of the present invention may also be removed and replaced from affected limbs to allow for washing and for examination by the physician. They may also be re-used as many times as desired.

Accordingly, the present provides a self-adhering, orthopedic splint capable of being conformed to the contours of a limb which comprises: an elongated, warp knit fabric having relatively stiff, inelastic monofilaments in the width direction and relatively flexible, inelastic yarns in the length direction, said monofilaments being interrupted by at least one hinged section running in the lengthwise direction; said fabric having firmly anchored to at least one surface thereof a layer of normally tacky, pressure sensitive adhesive.

Other objects and advantages of the present invention will become readily apparent to those skilled in the art as the specification proceeds to describe the invention with reference to the accompanying drawings, in which:

FIG. 1 illustrates the orthopedic splint as manufactured showing the hinged section and the relatively stiff inelastic monofilaments in the width direction wherein the stiff yarns have been "weft inserted."

FIGS. 2–5 illustrate various configurations of the splint wherein, for instance, in FIG. 2 the splint has been folded at a 90° angle; in FIG. 3 the splint has been folded back over itself in triangular fashion and in FIGS. 4 and 5 the splint has been folded over itself lengthwise employing the advantage of the hinged section.

FIG. 6 shows how support may be provided by covering hinged sections in offset fashion with further layers of fabric.

FIG. 7 shows a typical crisscrossed wrapping of a wrist wherein many triangles have been formed by folding the splint back over itself to provide additional support to specifically affected areas.

FIGS. 8 and 9 are point diagrams of the preferred fabric constructions for the splint.

Referring now to the drawings, FIG. 1 shows a section of the new and improved orthopedic splint 10 having relatively stiff inelastic monofilament yarns 12 running in the width direction and relatively flexible inelastic yarns 14 running in the length direction and further being provided with a hinged section 16 connecting warp knit strips 18 and 20. The hinged section 16 connects the warp knit strips by knit-in thread 22.

FIGS. 2–5 show desired configurations for the orthopedic splint of the present invention. In FIG. 2 the splint has been folded over itself to form a 90° angle 24 which is held in position by means of pressure sensitive adhesive in section 26. In FIG. 3 the fabric has been folded back over itself in offset fashion forming triangular section 27 which is held in place by means of pressure sensitive adhesive provided in section 28. In FIG. 4 the fabric has been folded over itself in lengthwise fashion showing the advantages of providing hinged section 16 in the fabric. FIG. 5 is a view along the pane shown in FIG. 4.

FIG. 6 illustrates overlapping of successive layers of the splint in offset fashion such that hinged sections in one layer of the fabric are covered with further layers of the fabric thereby providing increased support to affected areas.

FIG. 7 shows the new and improved orthopedic splint 10 wrapped around the wrist of an injured arm 30 and hand 32 to inhibit the flexing of the wrist. FIG. 7 is only one example of the use of the new and improved orthopedic splint because it can obviously be used on other portions of the body such as the leg to perform the same function. The splint consists of strips 18 and 20, which are knitted.

As briefly noted above, the splint of the present invention consists of one or more warped knit strips although only two strips, 18 and 20, are shown. These strips are connected together to form the desired splint width. Ideally, the connection of the desired number of strips 18 and 20 will be done automatically on a knitting machine.

As shown in FIG. 7, it is desired to hold the hand 32 substantially in line with the arm 30 to prevent flexing at the wrist, and to this end the individual strips 18 and 20 of the splint 10 are designed to provide a plurality of stiffening monofilaments in the width direction.

As shown in FIG. 7, the monofilament yarns 12 (shown in FIG. 1) in the splint portion around the wrist will lie in a plane substantially parallel to the arm 30 thereby, due to the stiffness of the yarn, prevent the hand 32 from flexing at the wrist. Furthermore, since the splint 10 is wrapped around the arm and hand, the yarns 12 probably will not lie on top of one another thereby providing further stiffness. Because the yarns selected for use in the lengthwise direction are relatively inelastic, the splint 10 under normal tension is to pulled tight enough to restrict the circulation of blood in the injured limb but can be so employed to provide the necessary support for the injured body member.

The fabric construction shown in FIGS. 8 and 9 is preferably knit on a Raschel warp knitting machine having at least five guide bars to form the desired characteristics in the fabric. A wide width of fabric is knit with each strip 18 and 20 encompassing fifteen needles in the wale direction with the overall design repeating every two courses. FIG. 8 is a point diagram of the individual strips or bands 18 and 20.

In forming the fabric of the following drawings, the following bar movement patterns are employed.

1=2-0, 0-2
2=2-4, 2-0
3=30—30, 0—0
4=24—24, 0—0
5=30—30, 0—0

Textured polyester yarns (150 denier) 14 are provided at bar 1. These yarns actually have some stretch but the finishing process renders them essentially inelastic which is the characteristic desired in the final product.

Tricot stitch 34 is made with 150 denier textured polyester (bar #2) to give a "cushion" effect on the edges of the splint 10, to prevent monofilament yarns 12 from sliding out at the edges and an extra yarn 38 shown in FIG. 9 may be provided in the same bar if tapes are to be combined on the knitting machine.

In a preferred embodiment the strips 18 and 20 may be knitted as a wide panel comprising multiple strips, e.g. 50 to 70 tapes or even strips may be slit into individual splints each containing at least two strips and at least one hinged section 16.

As disclosed in the preferred embodiment, the tape is basically knit using five bars (1 through 5) with bars 1 and 2 knitting and bars 3 through 5 laying in yarns but obviously if desired the tape can be knit with only one bar and one bar laying in monofilament or other yarns.

Monofilament yarn (750 denier and 10.9 mil polyester) 12 is sandwiched between 2 ends 40 and 42 of 150 denier textured polyester yarns in bars 3 and 5 in a sinusoidal path throughout the length of the splint to provide rigidity in the course or width direction. The monofilament may be from about 2 mils to about 20 mils. Diameters of less than 2 may not provide necessary rigidity and diameters in excess of 20 mils may be undesired from a manufacturing standpoint. The rigidity of the monofilament prevents the splint 10 from bending or flexing when in use. To provide added comfort to the patient the monofilament may be reversed at a point which is at a greater distance inward from the edge of the strips 18 and 20 than the reversal point shown in the drawing. Also, more ends may be added in bar number 2 to make a wider selvage to provide a further cushioning effect.

In addition to the five bars shown in FIG. 8 one or more additional bars may be employed to knit in added yarn (150 denier textured polyester) to provide a smooth surface next to the skin.

The greige fabric which has been knitted as described above may be finished using conventional finishing techniques. In order to enhance breathability of the fabric as well as fluid transfer away from the skin it may be desired to blow high velocity air through the fabric immediately after padding of the finishing chemicals and prior to drying.

It is noted that the adhesive employed in connection with the splint of the present invention may include a wide range of pressure sensitive adhesives although acrylic adhesives are preferred.

Although the specific embodiment of the invention has been described, it is contemplated that many changes may be made without departing from the spirit or scope of the invention which is further defined by the claims appended hereto.

I claim:

1. A self-adhering, orthopedic splint capable of being conformed to the contours of a limb, which comprises: an elongated, inelastic, warp knit fabric having relatively stiff, inelastic monofilaments in the width direction and relatively flexible, inelastic yarns in the length direction, said monofilaments being interrupted by at least one hinged section running in the lengthwise direction; said fabric having firmly anchored to at least one surface thereof a layer of normally tacky, pressure sensitive adhesive.

2. The self-adhering splint of claim 1 wherein said relatively stiff inelastic monofilaments are polyester of from about 2 to about 20 mils in thickness.

3. The self-adhering orthopedic splint of claim 2 wherein said relatively flexible inelastic yarns are polyester yarns. smooth surface next to the skin.

4. The self-adhering orthopedic splint of claim 1 wherein said relatively stiff inelastic monofilaments have been sandwiched between said relatively flexible inelastic yarns in a sinusoidal path throughout the length of said splint.

5. The self-adhering orthopedic splint of claim 4 wherein the reversal point for said sinusoidal path of said relatively stiff inelastic mono-filaments is remote from the edge of said splint to provide a cushioning effect.

6. The self-adhering orthopedic splint of claim 5 wherein a tricot stitch is provided on th edges of said splint to provide a cushioning effect.

* * * * *

UNITED STATES PATENT AND TRADEMARK OFFICE
CERTIFICATE OF CORRECTION

PATENT NO.   :   4,798,200
DATED        :   January 17, 1989
INVENTOR(S)  :   Warthen et al.

It is certified that error appears in the above-identified patent and that said Letters Patent is hereby corrected as shown below:

Column 1, line 4, after "self-adhering" insert --splint capable of--

Column 1, line 21, after "bulky" insert --and--

Column 1, line 46, after "present" insert --invention--

Column 2, line 67, the word "to" should be "not"

Column 3, line 31, after the word "even" insert "more and the"

Column 4, line 51, the word "th" should be "the"

Signed and Sealed this

Tenth Day of July, 1990

*Attest:*

HARRY F. MANBECK, JR.

*Attesting Officer*     *Commissioner of Patents and Trademarks*